United States Patent [19]

Stephens et al.

[11] Patent Number: 5,292,339
[45] Date of Patent: Mar. 8, 1994

[54] IMPLANTABLE PACEMAKER/CARDIOVERTER/DEFIBRILLATOR DEVICE AND METHOD INCORPORATING MULTIPLE BRADYCARDIA SUPPORT PACING RATES

[75] Inventors: Anthony C. Stephens, Willoughby; Stephen G. Wilson, Stanmore, both of Australia

[73] Assignee: Telectronics Pacing Systems, Inc., Englewood, Colo.

[21] Appl. No.: 875,777

[22] Filed: Apr. 29, 1992

[30] Foreign Application Priority Data

Jun. 14, 1991 [AU] Australia ................... 6715

[51] Int. Cl.$^5$ ................................ A61N 1/00
[52] U.S. Cl. .................................... 607/15
[58] Field of Search ........ 128/419 D, 419 P, 419 PG; 607/5, 9, 14, 15

[56] References Cited

U.S. PATENT DOCUMENTS

| | | | |
|---|---|---|---|
| 3,857,398 | 12/1974 | Rubin | 128/419 D |
| 4,869,252 | 9/1989 | Gilli | 128/419 PG |
| 4,895,151 | 1/1990 | Grevis et al. | 128/419 PG |
| 4,940,054 | 7/1990 | Grevis et al. | 128/419 PG |
| 4,998,974 | 3/1991 | Aker | 128/419 PG |
| 5,161,527 | 11/1992 | Nappholy et al. | 128/419 D |

FOREIGN PATENT DOCUMENTS 0161140 11/1985 European Pat. Off. .
WO8901802 3/1989 PCT Int'l Appl. .

*Primary Examiner*—Lee S. Cohen
*Assistant Examiner*—Marianne Parker
*Attorney, Agent, or Firm*—Gottlieb, Rackman & Reisman

[57] ABSTRACT

An implantable cardioverting/defibrillating pacemaker and method for treating arrhythmias of a patient's heart are disclosed. Bradycardia support pacing is initially provided at a normal standby rate, in the absence of a tachycardia. Upon detection and confirmation of a tachycardia, antitachycardia therapy in the form of antitachycardia pacing pulse therapy and/or cardioversion or defibrillation therapy is delivered to the heart. Thereafter, upon reversion of the tachycardia, bradycardia support pacing is again delivered to the heart but at a greater rate than the earlier normal standby rate and only for a predetermined time period. At the end of such time period, the bradycardia support pacing rate is returned to the normal standby rate, either directly or in decremental steps.

33 Claims, 4 Drawing Sheets

IMPLANTABLE PACEMAKER/CARDIOVERTER/DEFIBRILLATOR DEVICE AND METHOD INCORPORATING MULTIPLE BRADYCARDIA SUPPORT PACING RATES

TECHNICAL FIELD

This invention relates to implantable medical devices which deliver energy to cardiac tissue in an attempt to revert tachycardia and restore a normal sinus rhythm to a patient, and, more particularly, to those of such devices which are provided with multiple bradycardia support pacing rates.

BACKGROUND ART

Implantable pacemaker/defibrillator devices are well known to the medical profession. One early example of such a device is U.S. Pat. No. 3,857,398 to L. Rubin. The Rubin device utilizes separate circuitries in dealing with the different functions of pacing and defibrillation. There is no provision in the Rubin device for changing the bradycardia standby rate. All of Rubin's bradycardia pacing pulses are apparently delivered at the same rate. Many advances have been made after Rubin in the development of devices and techniques for providing effective medical responses to a variety of heart disorders of arrhythmias.

Recent efforts have resulted in the development of more sophisticated implantable pacing and defibrillating devices. One example of such a device is disclosed in U.S. Pat. No. 4,869,252 to N. L. Gilli, entitled "Apparatus and Method for Controlling Pulse Energy in Antitachyarrhythmia and Bradycardia Pacing Device". This Patent discloses an apparatus which provides bradycardia support pacing at different energy levels, including a higher pulse energy for a period following successful antitachycardia therapy, and a lower level during normal bradycardia support pacing. Capture is more efficient at the higher energy level since the heart has been traumatized by the tachycardia and/or the antitachycardia therapy. In the Gilli patent, again, the bradycardia therapy is delivered at a constant programmed standby rate.

The implantable pacing and defibrillating device disclosed in U.S. Pat. No. 4,940,054 to R. Grevis et al., entitled "Apparatus and Method for Controlling Multiple Sensitivities in Arrhythmia Control System Including Post Therapy Pacing Delay," is another example of a more sophisticated device of this type. Following antitachycardia therapy, which may be antitachycardia pacing or cardioversion/defibrillation, there is a pause or post therapy delay for a period of time substantially greater than a normal standby interval prior to the commencement of bradycardia support pacing. However, when bradycardia support pacing is required after antitachycardia therapy, it is delivered at a constant rate.

A problem that is common to all existing antitachyarrhythmia devices is their failure, after reverting tachycardias, to compensate patients who are dependent on bradycardia support pacing for the hemodynamic compromise resulting from the tachycardia and/or the antitachycardia therapy.

A tachycardia and/or antitachycardia therapy can temporarily reduce the heart's pumping efficiency. If so, the hemodynamic competence of a bradycardia support pacing-dependent patient being paced at a constant standby rate is impaired for as long as the pumping efficiency remains reduced. This can be traumatic to a patient and presents a real problem to some patients that are currently using existing devices.

It is therefore a primary object of the present invention to provide an improved apparatus and a method for treating cardiac arrhythmias which, following reversion from tachycardia, compensate for hemodynamic compromise experienced during tachycardia and/or following antitachycardia therapy.

It is a further object of the invention to provide an improved apparatus and method for treating cardiac arrhythmias which delivers antitachycardia pacing therapy and cardioversion/defibrillation therapy when needed and includes temporarily increasing the bradycardia support pacing rate following the delivery of antitachycardia therapy.

Further objects and advantages of this invention will become apparent as the following description proceeds.

SUMMARY OF THE INVENTION

In accordance with the principles of the present invention, the bradycardia support pacing standby rate is automatically increased from one normal value to another, higher, programmed value after reversion of a tachycardia has been detected. The standby rate of normal bradycardia support pacing therapy is a programmable parameter in the antitachyarrhythmia devices disclosed in U.S. Pat. Nos. 4,869,252 and 4,940,054, referred to above, but remains at a fixed value for a particular patient for all such therapy delivered to that patient. In the present invention, the bradycardia support pacing standby rate following the delivery of antitachycardia therapy remains at a value which is higher than the normal standby value for a predetermined time interval, the length of which may also be made a programmable parameter, before returning eventually to the patient's normal bradycardia support pacing standby rate.

Additionally, in accordance with the invention, there is provided an apparatus for treating cardiac arrhythmias comprising means for delivering bradycardia pacing pulses, means for detecting tachycardias, means for delivering antitachycardia therapy following detection of a tachycardia, means for confirming the absence of tachycardia following the delivery of the antitachycardia therapy, means for delivering post-reversion bradycardia support pacing pulses for a predetermined time period at a higher than normal standby rate immediately following such antitachycardia therapy and, following the expiry of the predetermined time period, thereafter delivering bradycardia support pacing pulses at the normal standby rate.

Additionally, the invention provides a method for treating cardiac arrhythmias comprising the steps of delivering bradycardia pacing pulses, detecting the presence of tachycardia, delivering antitachycardia therapy following detection of a tachycardia, confirming the absence of tachycardia following the delivery of the antitachycardia therapy, delivering post-reversion bradycardia support pacing pulses for a predetermined time period at a higher than normal standby rate immediately following the antitachycardia therapy, and, at the expiry of the predetermined time period, thereafter delivering bradycardia support pacing pulses at the normal standby rate.

BRIEF DESCRIPTION OF THE DRAWINGS

While the specification concludes with claims particularly pointing out and distinctly claiming the subject matter regarded as the invention herein, it is believed that the present invention will be more readily understood upon consideration of the following detailed description, taken in conjunction with the accompanying drawings, in which:

BEST MODE FOR CARRYING OUT THE INVENTION

As used herein, the term "antitachycardia pacing" includes any pacing used for the reversion of tachycardia. The term "tachycardia" refers to any fast abnormal rhythm of the heart which may be amenable to treatment by electrical discharges, and specifically includes ventricular tachycardia (VT), supraventricular tachycardia (SVT), ventricular flutter and/or ventricular fibrillation (VF).

The term "therapy" as used herein includes the processes used between the detection and reversion of a tachyarrhythmia and includes the actions of antitachycardia pacing, cardioversion shock and defibrillation shock. The term "cardioversion" refers to the discharge of electrical energy into cardiac tissue in an attempt to terminate or revert a tachyarrhythmia. This may take the form of a high energy discharge (up to 40 Joules or more) or a low energy charge (less than 1 Joule). Cardioversion shocks may or may not be synchronized to the rhythm of the heart. Defibrillation is a particular example of cardioversion.

This invention applies equally to devices which deliver energy synchronized to an R-wave and to those that do not, and applies to devices which use lower energy pulses (up to 1 Joule) as well as to devices which use higher energy pulses (up to 40 Joules or more). The invention applies to devices which deliver cardioverting shocks alone, as well as to devices which deliver antitachycardia pacing pulses alone or in a combination with cardioverting shocks. The invention will usually apply to ventricular implantable cardioverters, but is equally applicable to atrial cardioverters or multiple chamber cardioverters or defibrillators. The invention applies also to the delivery of any antitachycardia pacing pulse and post-reversion pacing therapy.

Figure 1:
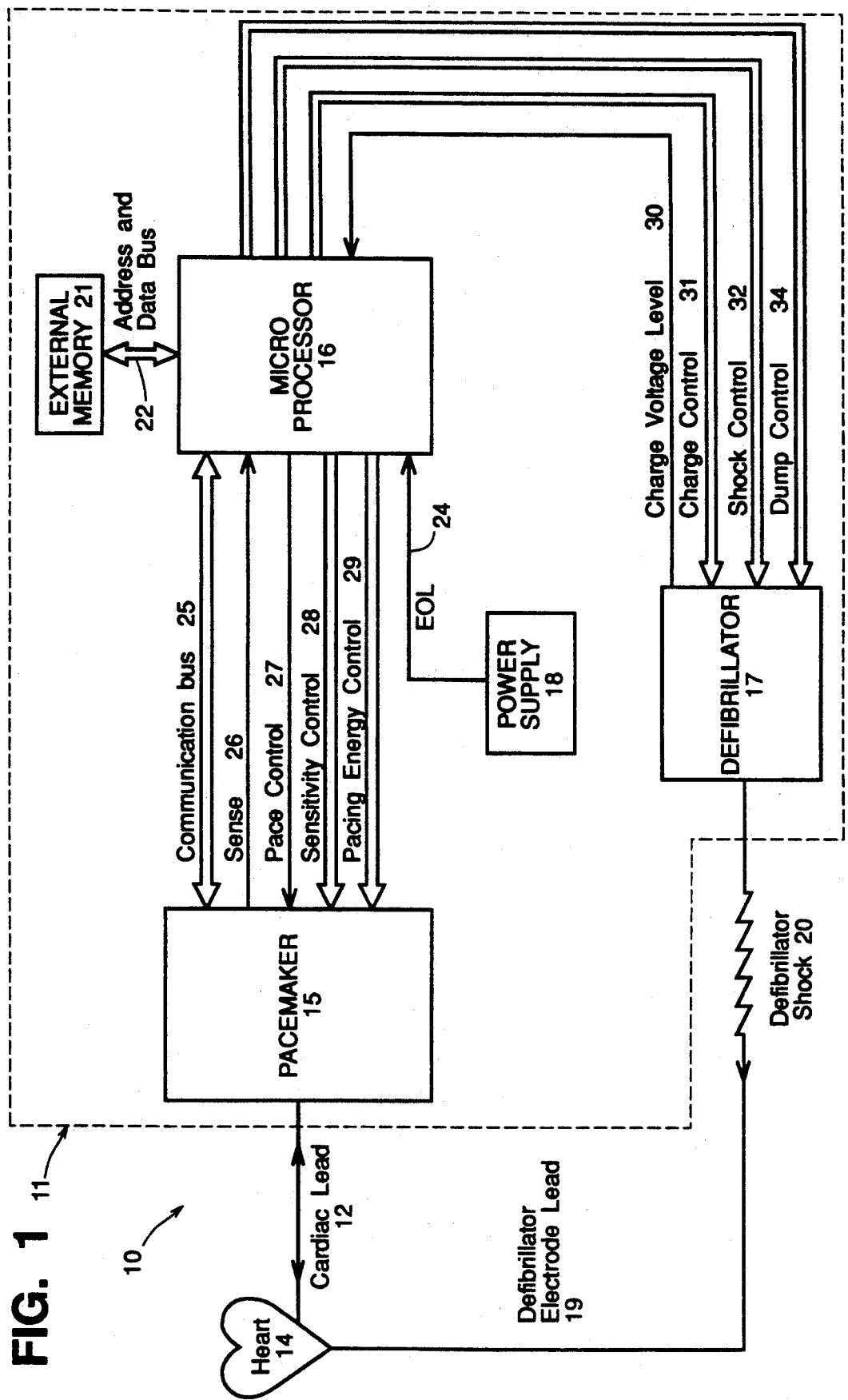
FIG. 1 is a block diagram of an arrhythmia control system in which the present invention may be used.

Referring to FIG. 1, there is depicted a block diagram of an arrhythmia control system 10. System 10 is designed to be implantable and includes a pulse module 11 and appropriate leads. More particularly, system 10 will generally include: a cardiac lead 12 connected to the patient's heart 14; a pacemaker 15 for the detection of analog signals representing cardiac electrical activity and for the delivery of pacing pulses to the heart; a microprocessor 16 which, in response to various inputs received from the pacemaker 15 as well as from a defibrillator 17, performs various operations so as to generate different control and data outputs to both pacemaker 15 and defibrillator 17; and a power supply 18 for the provision of a reliable voltage level to pacemaker 15, microprocessor 16 and defibrillator 17 by suitable electrical conductors (not shown). Defibrillator 17 produces a high voltage to charge its capacitors and then discharges them in response to control signals from microprocessor 16. A defibrillator electrode lead 19 transfers the energy of a defibrillator shock 20 from the implanted pulse module to the surface of the heart 14.

Microprocessor 16 is connected to an external memory 21 by an address and data bus 22. An end-of-life (EOL) signal line 24 is used to provide, to microprocessor 16, a logic signal indicative of the approach of battery failure in power supply 18.

As more fully described below, microprocessor 16 and pacemaker 15 are connected by a communication bus 25, a sense line 26, a pace control line 27, a sensitivity control bus 28, and a pacing rate control bus 29. As also more fully described below, microprocessor 16 is connected to defibrillator 17 by a charge voltage level line 30, a charge control bus 31, a shock control bus 32, and a dump control bus 34.

Figure 2:
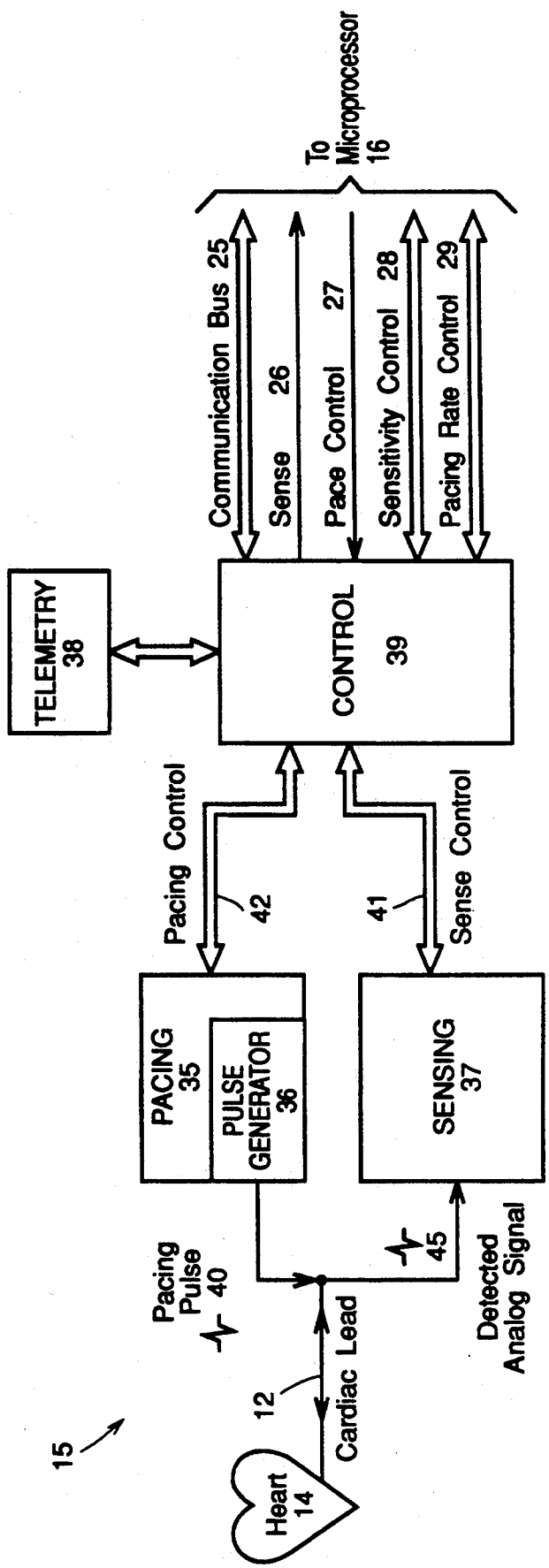
FIG. 2 is a block diagram of a pacemaker utilized in FIG. 1.

Referring to FIG. 2, pacemaker 15 comprises pacing circuit 35 which includes a pacing pulse generator 36, sensing circuit 37, and telemetry circuit 38. In addition, there is a control block 39 which includes an interface to microprocessor 16.

In operation, sensing circuit 37 detects analog signals 40 from the heart 14 and converts the detected signals to digital signals. In addition, sensing circuit 37 receives an input sense control signal (which determines the sensitivity of the detection circuits in sensing circuit 37) by way of a sense control bus 41 from control block 39. A change in this sensitivity will affect the voltage deviation required at the sensing electrode for a sense to be registered in sensing circuit 37. The operation of the logic which changes the sensitivity is described in more detail in the aforementioned U.S. Pat. No. 4,940,054.

Pacing circuit 35 also receives inputs from control block 39, including a pace control and a pacing rate control by way of pacing control bus 42 which carries the signals on pace control line 27 and pacing rate control bus 29. The pace control determines the type of pacing to occur and the bradycardia standby rate is established by the pacing rate control. Pacing circuit 35 causes pulse generator 36 to generate pacing pulses 44 which are delivered to the patient's heart 14 by means of cardiac lead 12.

Telemetry circuit 38 provides a bi-directional link between control block 39 of pacemaker 15 and an external device such as an external programmer (not shown). It allows data such as the operating parameters to be read from or altered in the implanted pulse module 11 (FIG. 1).

Figure 3:
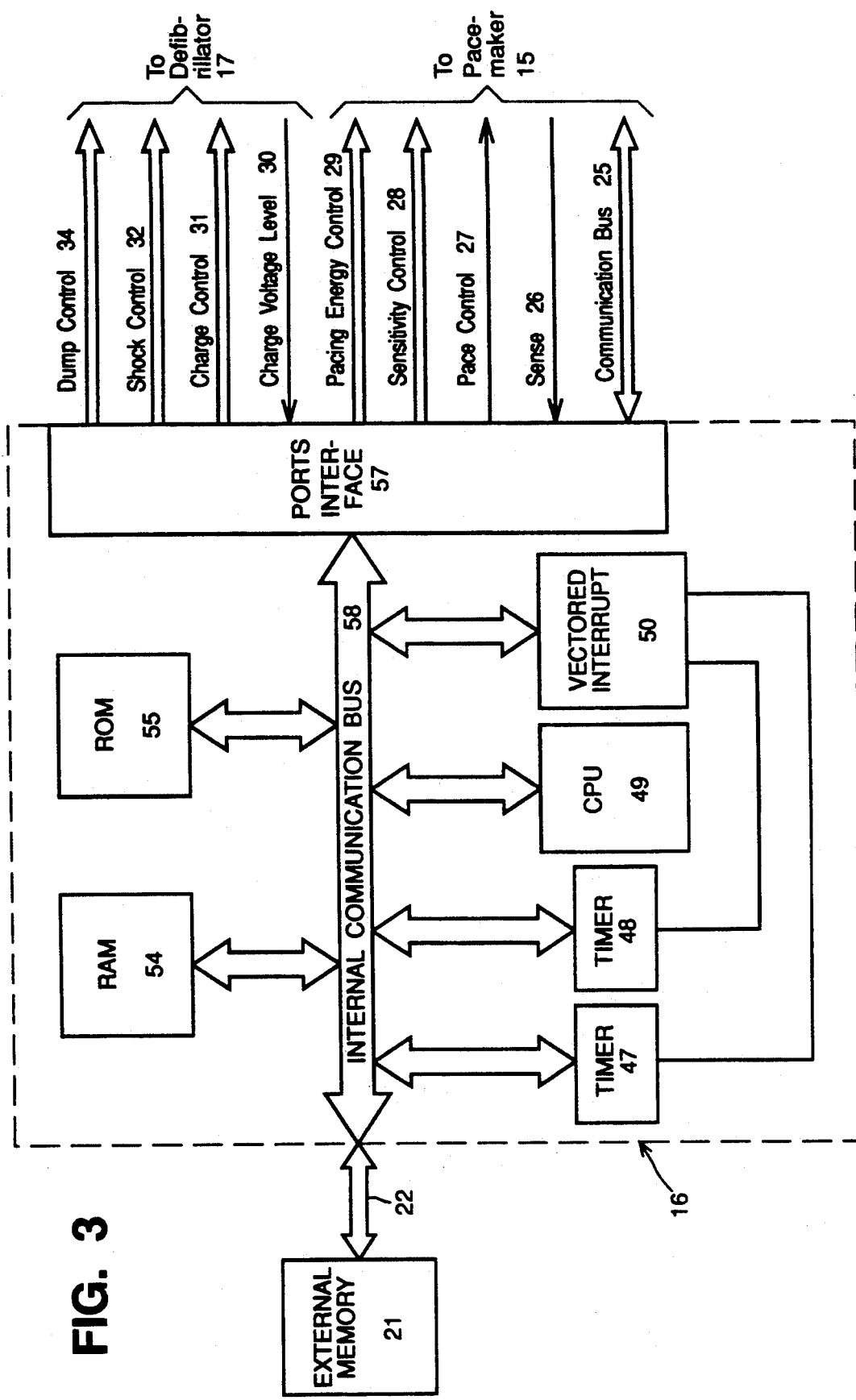
FIG. 3 is a block diagram of a microprocessor utilized in FIG. 1.

Referring to FIG. 3, microprocessor 16 comprises two 16-bit timers 47 and 48, a CPU 49, a vectored interrupt block 50, a RAM 54, a ROM 55, a ports interface 57 and an internal communication bus 58. RAM 54 acts as a scratch pad memory during execution of the various programs stored in ROM 55 and used by microprocessor 16. These programs include system supervisory programs, detection algorithms, and programming implementing the logic flow diagram of FIG. 4, as well as storage programs for storing, in external memory 21, data concerning the functioning of module 11 and the electrogram provided by cardiac lead 12. Timers 47 and 48 and associated control software implement some timing functions required by microprocessor 16 without resorting entirely to software, thus reducing computational loads on and power dissipation by CPU 49.

Signals received from telemetry circuit 38 permit the external programmer to change the operating parameters of pacemaker 15 by supplying appropriate signals to control block 39. Communication bus 25 serves to provide signals indicative of such control to microprocessor 16. Thus, it is also possible for an external programmer to control operation of defibrillator 17 by means of signals provided to microprocessor 16.

Appropriate telemetry commands may cause telemetry circuit 38 to transmit data to the external programmer. Data stored is read out, by microprocessor 16, on to communication bus 25, through control block 39 in pacemaker 15, and into telemetry circuit 38 for transmission to the external programmer by a transmitter in the telemetry circuit.

Microprocessor 16 receives various status and/or control inputs from pacemaker 15 and defibrillator 17. During normal pacer operations the input signal to pacemaker 15 is a sense signal on sense line 26 which is used by microprocessor 16 to perform operations such as arrhythmia detection. Microprocessor 16 produces outputs such as the pace control on pace control line 27 which determines the type of pacing to take place. Other pacemaker control outputs generated by microprocessor 16 include a pacing rate control signal on pacing rate control bus 29 which determines the bradycardia standby rate, and a sensitivity control signal on sensitivity control bus 28, which determines the sensitivity setting of the sensing circuit.

Microprocessor 16 provides to defibrillator 17 a shock control signal on shock control bus 32 which indicates that a shock is to be delivered to the patient, a dump control signal on dump control bus 34 which indicates that a shock is to be dumped at an internal load within defibrillator 17, and a charge control signal on charge control bus 31 which determines the voltage level of the shock to be delivered. Charge voltage level line 33 provides a digital signal representative of charge voltage from an analog to digital converter within defibrillator 17, thus providing a feedback loop which assures that a shock of proper energy level is delivered by defibrillator 17.

Figure 4:
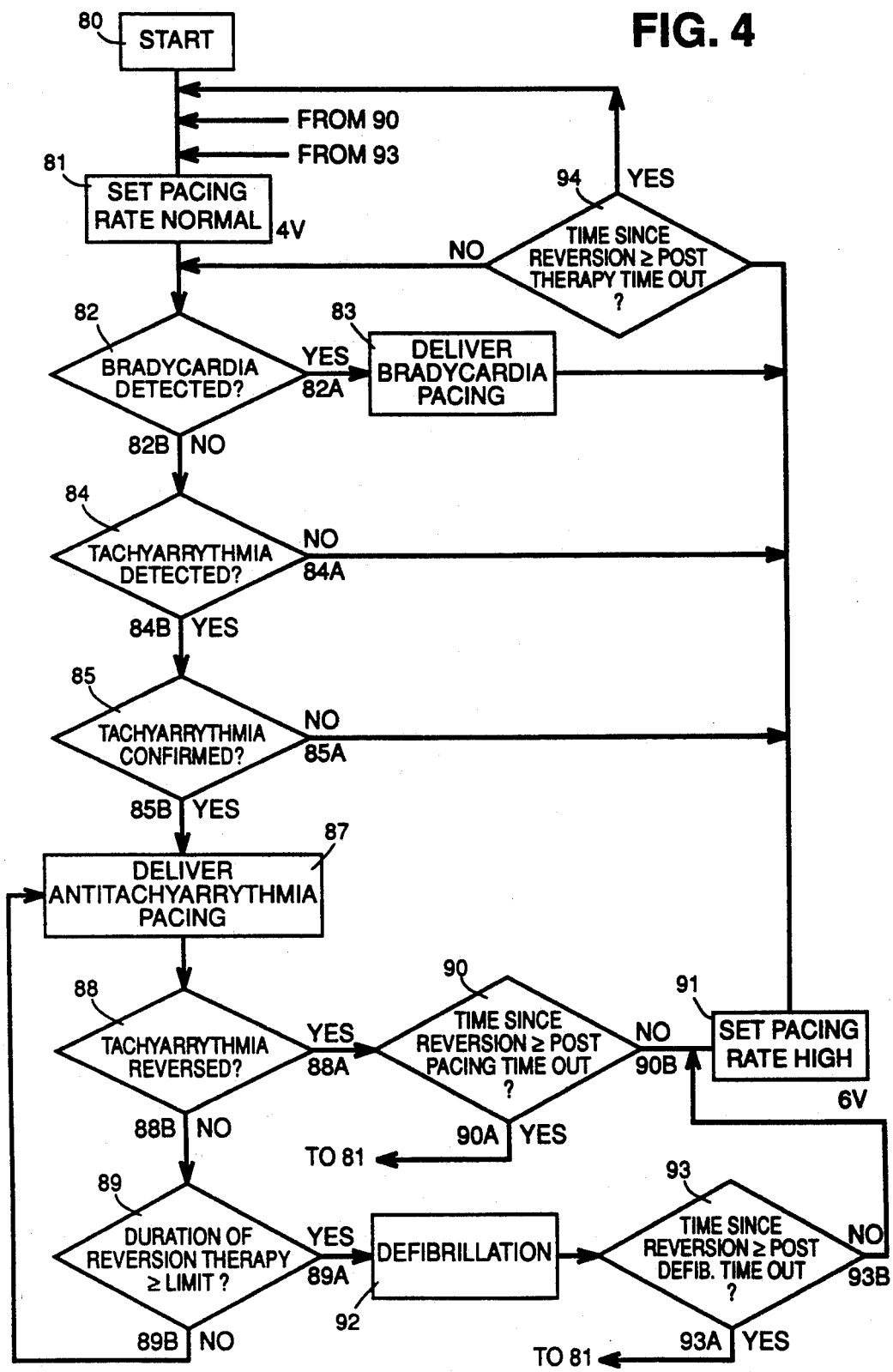
FIG. 4 is a logic flow diagram of software executed by the microprocessor of FIG. 3 in accordance with the present invention.

FIG. 4 is a logic diagram of the microprocessor flow control for changing pulse energies and pacing rates. The start is shown at 80, and at 81 the pacing rate is set to a predetermined programmed normal value. At 82 a determination is made as to whether a bradycardia condition exists. If it does, then bradycardia support pacing is delivered at this normal pacing rate, as shown at 83.

If there is no bradycardia condition, as shown at 82B, then branching occurs based on whether or not there is a tachyarrhythmia condition, as shown at 84. If there is no detection of a tachyarrhythmia condition, as shown at 84A, then the program proceeds to logic block 94 (to be described hereinafter) and either loops back through 82 or 80, depending on the decision made at 94. If a tachyarrhythmia condition is detected at 84, as shown at 84B, then a follow-up check is made for confirmation of the tachyarrhythmia, as shown at 85. If a tachyarrhythmia condition is not confirmed, as shown at 85A, then the program proceeds to logic block 94 and either loops back to 82 or 80, depending on the decision made at 94.

If a tachyarrhythmia condition is confirmed, as shown at 85B, then antitachyarrhythmia therapy is delivered to the patient, as shown at 87. Following delivery of such therapy, a determination is made at 88 as to whether or not the tachyarrhythmia has been reverted. If the tachyarrhythmia condition has not been reverted, as shown at 88B, then further antitachyarrhythmia therapy is delivered at 87. The therapy continues until reversion takes place at 88A, or for a given limited time, as determined at 89 and as more fully explained below.

Reversion of a tachyarrhythmia at 88A starts a post-pacing timer at 90. As long as the time elapsed following reversion does not exceed a predetermined time interval, the pacing rate is set to a predetermined programmed high value at 91 and it will remain at that high value until the expiration of the post-pacing timeout period at 90. The post-pacing timeout is a programmed period of time following antitachyarrhythmia pacing therapy during which the bradycardia pacing rate is set at the high programmed value in order to more quickly restore the patient to full hemodynamic competence. Programming may be performed by the physician just prior to implantation, and it may be changed after implantation through telemetry circuit 38.

If the pacing rate is at the high programmed value and the post-pacing timeout period is exceeded, as shown at 90A, a command is given to set the pacing rate back to the normal programmed value at 81. If the time since tachyarrhythmia reversion has not exceeded the post-pacing timeout period, or if the pacing rate has been set back to the normal value following the expiration of the post-pacing timeout period as shown at 90A, then at 82 branching occurs based on whether or not bradycardia has been detected. If a bradycardia condition is detected, as shown at 82A, then bradycardia support pacing is delivered, as shown at 83. This bradycardia support pacing will be delivered either at the high programmed rate if the post-pacing timeout period has not expired, or at the normal programmed rate value if the post-pacing timeout period has expired.

In any event, following reversion of the tachyarrhythmia condition, if the post-pacing timeout has not occurred, at 90B the pacing rate is set to the high programmed value, as shown at 91, and the program then proceeds to logic block 94 where, again, if the time since reversion is not equal to or greater than the post therapy time out, the loop passes back to 82. If the post therapy time out has occurred, the loop passes back to 81, via 94, and, also, at 90A of logic block 90, branching to 81 occurs. Accordingly, the pacing rate is set to normal.

If there has been no indication at 88 of reversion of the tachyarrhythmia and the time limit set at 89 for the duration of reversion therapy is exceeded, branching occurs to 89A and defibrillation shock therapy is applied at 92. A post-defibrillation timer at 93 is reset at this time, and the pacing rate is then set to the high programmed value, as shown at 93B and 91. The program then proceeds to logic block 94 where, again, if the time since reversion is not equal to or greater than the post therapy time out, the loop passes back to 82. If the post therapy time out has occurred, the loop passes back to 81, via 94, and, also, at 93A of logic block 93, branching to 81 occurs. Thus, again, the pacing rate is set to normal.

In FIG. 4, the timeouts for high rate bradycardia pacing may be different time intervals (as programmed into or fixed by the timers 90 and 93) depending upon whether antitachycardia has been reverted at 88 or defibrillation has occurred at 92. It is possible to implement a system wherein the same programmable timer is used in both cases by, for example, eliminating timer 93 and connecting the output of block 92 as an additional input to timer 90, which could then be called, generally, a post-therapy timer. In that case, the timeout interval would be programmed (or fixed) to be the same following both antitachycardia pacing therapy and defibrillation shock therapy.

It is also preferable that bradycardia support pacing be inhibited for programmable periods of time after reversion of a tachyarrhythmia by either antitachycardia pacing therapy or defibrillation shock therapy, so as to avoid any pro-arrhythmic effect. The use of such a delay is described in the aforementioned U.S. Pat. No. 4,940,054.

The time limit for the application of antitachyarrhythmia therapy at 87, determined at 89, is of importance. In this regard, reference is made to U.S. Pat. No. 4,895,151 to R. Grevis et al., entitled "Apparatus and Method for Therapy Adjustment in Implantable Cardioverter", the disclosure of which is incorporated herein by reference. This patent discloses an apparatus and method for treating tachyarrhythmias wherein upon detection of the presence of a patient tachyarrhythmia, a first antitachyarrhythmia therapy (antitachycardia pacing) is given at a first energy level. Concurrently, the hemodynamic condition (e.g., the average cardiac cycle length) of the patient is measured and a length of time to therapy switchover is continually derived during the application of the first antitachyarrhythmia therapy. The length of time to a therapy switchover is a function of the hemodynamic condition of the patient. When the time following detection of the patient tachyarrhythmia exceeds the length of time to switchover, a second antitachyarrhythmia therapy (a high energy shock) at a second energy level is provided.

It will be apparent from the foregoing description that the present invention provides an improved apparatus and method for treating cardiac arrhythmias in which, following reversion of tachycardia, hemodynamic compromise experienced during or following the tachycardia is compensated for by setting the bradycardia support pacing rate for any bradycardia support pacing delivered immediately following the reversion of the tachycardia to a higher than normal rate, for a predetermined time period following such reversion. It will also be apparent that the present invention is equally applicable to antitachyarrhythmia devices capable of delivering one or more cardioversion or defibrillation shocks, as well as to devices which deliver antitachycardia pacing pulses alone or in combination with cardioversion or defibrillation shocks. The antitachycardia pacing may be delivered to the atrium, the ventricle, or to both the atrium and the ventricle.

It will be understood that various other implementations of the invention are contemplated. For example, although the use of a microprocessor is disclosed herein, the operations of FIG. 4 may be implemented using hard-wired logic rather than software, as the distinction between hardware and software has become less significant. In general, engineering judgement, including considerations of conserving energy so as to prolong battery life, is exercised in deciding on a particular implementation of the invention for a given application.

Although the invention has been shown and described with reference to particular embodiments, it is to be understood that such embodiments are merely illustrative of the application of the principles of the invention. Numerous modifications may be made therein and other arrangements may be devised without departing from the broader aspects of this invention. It is, therefore, aimed in the appended claims to cover all such changes and modifications as fall within the true spirit and scope of this invention.

What is claimed is:

1. A method for treating a patient's malfunctioning heart comprising the steps of detecting episodes of bradycardia of the heart, delivering bradycardia support pacing to the heart at a first standby rate during episodes of bradycardia other than those that immediately follow reversion of a tachycardia, detecting tachycardia of the heart, reverting said tachycardia, delivering bradycardia support pacing to the heart at a second standby rate, greater than said first standby rate, during initial periods of episodes of bradycardia which immediately follow reversions of tachycardia, said initial periods being predetermined time periods, and delivering support pacing at said first standby rate upon expiration of said predetermined time periods during continuance of any episodes of bradycardia which follow reversions of tachycardia.

2. A method for treating arrhythmias of a patient's heart, comprising the steps of:
   delivering first bradycardia pacing pulses to the heart at a first programmed standby rate;
   detecting tachycardia of the heart;
   delivering antitachycardia therapy to the heart to revert said tachycardia; and
   delivering second bradycardia pacing pulses to the heart for a predetermined period of time, after reversion of said tachycardia, said second bradycardia pacing pulses being at a second programmed standby rate, said second standby rate being greater than said first standby rate.

3. The method of claim 2, wherein said antitachycardia therapy is a therapy selected from the group of therapies consisting of antitachycardia pacing therapy, cardioversion therapy and defibrillation therapy, and including the further step of selecting said selected antitachycardia therapy based on the tachycardia detected.

4. The method of claim 2, comprising the further step, after detection of said tachycardia, of confirming said detected tachycardia prior to supplying said antitachycardia therapy.

5. The method of claim 2, comprising the further steps of periodically ascertaining whether said tachyarrhythmia has been reverted, and terminating said antitachycardia therapy upon ascertaining that reversion of said tachycardia has occurred.

6. The method of claim 2, wherein said step of delivering antitachycardia therapy includes the sub-step of delivering antitachycardia pacing therapy to the heart.

7. The method of claim 2, wherein said antitachyarrhythmia therapy is initially antitachycardia pacing therapy, said antitachycardia pacing therapy is supplied for only a predetermined period of time, and, in the absence of a reversion of said tachycardia, said method includes the further step of changing said antitachycardia pacing therapy to defibrillation shock therapy after said predetermined period of time has elapsed.

8. The method of claim 2, including the further step, after said predetermined period of time, of delivering said first bradycardia pacing pulses at said first programmed standby rate.

9. The method of claim 2, wherein said antitachycardia therapy comprises a selected one of a plurality of treatments, and said method includes the further step, for each of said treatments, of determining said predetermined time independently of a determination thereof for other of said treatments.

10. The method of claim 2, comprising the further step of fixing said predetermined period of time.

11. The method of claim 2, comprising the further step of programming said predetermined period of time.

12. A method of treating arrhythmias of a patient's heart, comprising the steps of:
delivering first bradycardia pacing pulses to the heart at a first programmed standby rate;
detecting a tachycardia of the heart;
delivering antitachycardia pacing therapy to the heart to revert said tachycardia; and
delivering second bradycardia pacing pulses to the heart for a predetermined period of time after reversion of said tachycardia, said second bradycardia pacing pulses being of at least one other bradycardia pacing rate, said at least one other bradycardia pacing rate being greater than said first programmed standby rate.

13. An apparatus for treating arrhythmias of a patient's heart, comprising:
bradycardia pulse therapy means for a delivering bradycardia pacing pulses to the heart at a programmable standby rate;
detection means for detecting a tachycardia of the heart;
antitachycardia therapy means responsive to said detection means for delivering antitachycardia therapy to the heart to revert said tachycardia;
bradycardia pacing rate setting means for setting the rate of said bradycardia pacing pulses, said bradycardia pacing rate setting means initially setting said bradycardia pacing rate to a first programmed standby rate value prior to detection of said tachycardia and thereafter setting said bradycardia pacing rate to at least one other rate value for bradycardia pacing after detection and reversion of said tachycardia, said at least one other rate value being higher then said programmed standby rate value; and
timing means for causing said bradycardia pacing rate setting means to set the rate of said bradycardia pacing pulses to said at least one other rate value for a predetermined period of time.

14. The apparatus of claim 13, wherein said antitachycardia therapy means is selected from a group of antitachycardia therapy means consisting of an antitachycardia pacing pulse generator, a cardioverter, and a defibrillator.

15. The apparatus of claim 13, further comprising tachycardia confirmation means for confirming a detected tachycardia subsequent to the detection thereof, said antitachycardia therapy means being activated only after said tachycardia is confirmed by said tachycardia confirmation means.

16. The apparatus of claim 13, further comprising determining means for determining whether said tachycardia has been reverted, said determining means causing said antitachycardia therapy means to terminate said antitachycardia therapy when said tachycardia has been reverted.

17. The apparatus of claim 16, wherein said antitachycardia therapy means includes:
first therapy means for delivering antitachycardia pacing therapy to the heart; and
second therapy means for delivering electrical shock therapy to the heart if said determining means does not determine that tachycardia reversion has occurred within a predetermined time interval.

18. The apparatus of claim 13, wherein said antitachycardia therapy comprises a selected therapy from a group of therapies consisting of antitachycardia pacing therapy, cardioversion therapy and defibrillation therapy, wherein said at least one other rate value comprise two values, wherein one of said two values is set by said bradycardia pacing rate setting means following antitachycardia pacing therapy, and wherein the other of said two values is set by said bradycardia pacing rate setting means following defibrillation or cardioversion therapy.

19. The apparatus of claim 13, further comprising delay means for delaying delivery of said bradycardia pacing after said antitachycardia therapy means delivers said antitachycardia therapy.

20. The apparatus of claim 19, wherein said delay means delays said delivery of bradycardia pacing for a predetermined programmable time interval.

21. The apparatus of claim 13, wherein said first standby rate value comprises a normal pacing rate, said at least one other rate value comprises a post-reversion pacing rate, and wherein said bradycardia pacing rate setting means sets at least one intermediate bradycardia standby pacing rate between said post-reversion pacing rate and said normal pacing rate, thereby achieving a gradual resumption of the normal pacing rate following reversion of said tachycardia.

22. The apparatus of claim 21, wherein said bradycardia pacing rate setting means sets durations of each of said intermediate bradycardia standby pacing rates according to at least one programmable time delay.

23. The apparatus of claim 21, wherein said bradycardia pacing rate setting means sets durations of each of said intermediate bradycardia standby pacing rates according to at least one programmable number of bradycardia pacing pulses to be delivered at each of corresponding ones of said intermediate pacing rates.

24. The apparatus of claim 21, wherein said bradycardia pacing rate setting means resumes said normal pacing rate following a further period of gradually decreasing pacing rates, rather than upon expiration of said post-reversion period of time.

25. The apparatus of claim 24, wherein said bradycardia pacing rate setting means sets said further period of gradually decreasing pacing rates as a programmable number of pacing pulses.

26. The apparatus of claim 24, wherein said bradycardia pacing rate setting means derives said further period of gradually decreasing pacing rates from a programmed decrement in the bradycardia standby pacing rate applied to successive pacing pulses.

27. The apparatus of claim 24, wherein said bradycardia pacing rate setting means derives said further period of gradually decreasing pacing rates from a programmed increment in bradycardia standby pacing intervals applied to successive pacing pulses.

28. The apparatus of claim 24, wherein said bradycardia pacing rate setting means sets said further period of gradually decreasing pacing rates as a programmed time period.

29. The apparatus of claim 13, further comprising means for setting said period of time as a fixed time interval.

30. The apparatus of claim 13, further comprising programming means for programming said predetermined period of time.

31. The apparatus of claim 13, wherein after said predetermined period of time said timing means causes said bradycardia pacing rate setting means to again deliver said bradycardia pacing pulses at said first programmed standby rate value.

32. The apparatus of claim 13, wherein said antitachycardia therapy comprises a therapy selected from the group of therapies consisting of antitachycardia pacing therapy, cardioversion therapy and defibrillation therapy, and wherein said timing means comprises a plurality of timers, each of said timers being responsive to a delivery of one of said antitachycardia therapies by said antitachycardia therapy means, each of said timers causing a setting of said at least one other rate value to be for a period of time that is independent of the settings thereof caused by the others of said timers.

33. An apparatus for treating arrhythmias of a patient's heart comprising:
   bradycardia pulse delivering means for delivering bradycardia pacing pulses to the heart at a standby rate;
   detection means for detecting a tachycardia of the heart;
   antitachycardia therapy pacing means responsive to said detection means for supplying antitachycardia pacing therapy to the heart to revert said tachycardia;
   standby rate setting means responsive to said detection means for setting said standby rate of said bradycardia pacing pulses, said standby rate setting means setting said standby rate to a first programmed standby rate for normal bradycardia pacing, and to a second programmed standby rate for post-antitachycardia therapy bradycardia pacing; and
   timing means for causing said standby rate setting means to set said second programmed standby rate for a predetermined period of time.

* * * * *